(12) United States Patent
Hikichi et al.

(10) Patent No.: US 7,405,824 B2
(45) Date of Patent: Jul. 29, 2008

(54) OPTICAL COUPLING SYSTEM OF LIGHT MEASURING DEVICE AND SAMPLE

(75) Inventors: Naoko Hikichi, Tokyo (JP); Kenichi Nakama, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 3 days.

(21) Appl. No.: 11/558,059

(22) Filed: Nov. 9, 2006

(65) Prior Publication Data

US 2007/0127020 A1 Jun. 7, 2007

(30) Foreign Application Priority Data

Nov. 10, 2005 (JP) ............................. P2005-326032

(51) Int. Cl.
*G01J 3/30* (2006.01)
(52) U.S. Cl. ...................................... 356/317; 356/246
(58) Field of Classification Search .................. 356/317
See application file for complete search history.

(56) References Cited

U.S. PATENT DOCUMENTS

| | | | | |
|---|---|---|---|---|
| 5,112,215 A | * | 5/1992 | Frish et al. | 356/417 |
| 6,608,671 B2 | * | 8/2003 | Tsien et al. | 422/82.08 |
| 2003/0174325 A1 | * | 9/2003 | Zhang et al. | 356/318 |
| 2003/0191398 A1 | * | 10/2003 | Motz et al. | 600/478 |

FOREIGN PATENT DOCUMENTS

JP 11-326210 11/1999

* cited by examiner

*Primary Examiner*—Kara Geisel
(74) *Attorney, Agent, or Firm*—Whitham Curtis Christofferson & Cook, P.C.

(57) ABSTRACT

A light measuring device is designed, so that excitation light, emitted by a light source, is guided through an excitation light optical fiber to irradiate a sample, and that fluorescence discharged by the sample is guided to an optical detection system through a receiving light optical fiber. A coupling lens is arranged ahead of the excitation light optical fiber and ahead of the receiving light optical fiber on the sample side. A sample container for retaining a sample is so designed that a lens portion, for collecting excitation light and fluorescence, is integrally formed with the cylindrical bottom. According to this arrangement, excitation light is changed to parallel light or converged light by the coupling lens, and is collected at the sample by the lens portion integrally formed with the bottom of the sample container.

5 Claims, 5 Drawing Sheets

— EXCITATION LIGHT
----- FLUORESCENCE

OPTICAL COUPLING SYSTEM OF LIGHT MEASURING DEVICE AND SAMPLE

BACKGROUND OF THE INVENTION

1. Field of the Invention

The present invention relates to an optical coupling system comprising a light measuring device and a sample. More specifically, the present invention relates to an optical coupling system wherein a coupling lens is arranged ahead of an optical fiber and a lens portion is integrally formed at the bottom of a sample container, and excitation light, transmitted by the optical fiber, is efficiently coupled with the sample by the coupling lens and the lens portion, and an optical coupling system wherein light generated by a sample is efficiently coupled with an optical fiber by a lens portion and a coupling lens. This technology can be applied for a light measuring device, for example, that irradiates a sample with excitation light, and measures the intensity of fluorescence generated by the excited sample.

2. Related Art

As a technique that physically or chemically examines or analyzes a material, a light measuring device is available that excites a sample through the radiation of light, and measures light generated by the excited sample to obtain various data concerning the sample. Example light measuring devices are an apparatus that measures the intensity of fluorescence having a specified wavelength that is emitted by an excited sample, or that measures a transient change in fluorescence and detects a specified material or monitors a change in density, and an apparatus that measures the spectrum of fluorescence emitted by a sample to perform a quantitative or qualitative analysis. Since both apparatuses are capable of conducting highly sensitive measurements and are appropriate for the performance of microanalysis, they are widely employed. When a liquid sample is used, during the measurement process the sample is retained in a transparent sample container that permits irradiation with an excitation light and fluorescence.

For these light measuring devices, excitation light is projected onto a sample that is positioned at a location to which light from a light source is emitted, and fluorescence generated by the excited sample is appropriately collected and enters an optical detection system. Recently, another structure has been proposed wherein, using an optical fiber, excitation light is transmitted to a sample through a coupling lens, and by using another optical fiber, fluorescence output by the sample is guided through the coupling lens to an optical detection system (see, for example, JP-A-11326210). When the optical fibers are employed in this manner, the degree of freedom is increased for the positional relationships of the sample, the light source and the optical detection system. Further, since the fluorescence to be detected is transmitted through the optical fiber, disturbance light seldom enters the optical system, so that the sensitivity of an analysis of the fluorescence, which in many cases is weak, can be increased.

However, according to the conventional example, fluorescence cannot be efficiently extracted from a sample. As one reason, fluorescence output by the sample container is dispersed. As another reason, since there is a long distance between the sample and the coupling lens, it is difficult for fluorescence to be collected at the coupling lens, and since the irradiation area for excitation light is large and the radiation density is low, the surface emission of fluorescence occurs. Further, in the conventional example, a sample cannot be irradiated efficiently using excitation light. The reason for this is that since an excitation light optical fiber, that has a comparatively large diameter is employed in order to increase the intensity of the excitation light, the excitation light can not be controlled by a coupling lens and directed to a predetermined location for a sample, and thus, the radiation density of the excitation light is lowered.

Additionally, in the conventional example, since the amount of excitation light and the amount of fluorescence are increased as much as possible, an optical fiber having a large diameter, or multiple optical fibers, must be employed, and accordingly, the diameter of the coupling lens must be increased, and to connect the excitation light with the fluorescence, a plurality of lenses are required. Thus, the size of the optical system is increased.

SUMMARY OF THE INVENTION

The objective of the present invention is to efficiently irradiate a sample with excitation light, and to efficiently couple, with an optical fiber, light discharged by the sample.

To achieve this objective, according to the present invention, there is provided an optical system coupling a light measuring device and a sample, wherein excitation light emitted by a light source is guided through an excitation light optical fiber to irradiate the sample, and excited light emitted by the sample is guided to an optical detection system through a receiving light optical fiber, the optical system comprising:

a light measuring device including
  an excitation light optical fiber for guiding an excitation light to irradiate a sample,
  a receiving light optical fiber for receiving excited light from the sample, and
  a coupling lens arranged on a sample side of the excitation light optical fiber and the receiving light optical fiber; and a sample container including a cylindrical body for retaining the sample to which the excitation light is irradiated, and
  a lens portion integrally formed on a bottom of the cylindrical body for collecting the excitation light and the light emitted from the sample;

wherein the excitation light is changed to parallel light or converged light by the coupling lens and collected at the sample by the lens portion. The present invention can be applied not only for measuring fluorescence, but also for measuring any other type of light, such as phosphorescence, emitted by a sample that is irradiated with excitation light.

According to an example structure for the optical system provided for the light measuring device, an optical fiber bundle is formed of a single, centered excitation light optical fiber and a plurality of receiving light optical fibers surrounding this optical fiber, a capillary is attached to the distal end of the optical fiber bundle, and a coupling lens is inserted into, positioned within the capillary, and used both for excitation light and for receiving light. As another example structure, one excitation light optical fiber and another receiving light optical fiber may be adjacently fixed through a ferrule, a capillary may be attached to the distal ends of the optical fibers, and a coupling lens, used both for excitation light and for receiving light, may be inserted into and fixed within the capillary. It is preferable that the outer diameter of the optical fiber bundle be smaller than the diameter of the coupling lens, and that the diameter of the excitation light optical fiber be equal to or smaller than the diameter of the receiving light optical fiber. The coupling lens and the lens portion at the bottom of the sample container are arranged at a distance to prevent the formation of a light collecting point between them.

Normally, the sample container has a cylindrical body, but it may have a square barrel shape. And typically, the lens portion at the bottom of the cylindrical member is semispherical.

According to the invention, in the optical coupling system of the light measuring device and the sample, the lens portion, for collecting excitation light and fluorescence, is integrally formed with the bottom of the sample container in which the sample is retained, so that parallel light or converged light, obtained by the coupling lens, is collected at the sample by the coupling lens. Therefore, excitation light can be radiated, and fluorescence can be efficiently extracted. That is, as the effects provided by this invention, since the irradiation of excitation light can be concentrated more at the sample by using the lens portion, the radiation density of excitation light is increased, so that the amount of light output by the sample is increased. Further, since the state of fluorescence can be similar to the state of a point source in consonance with the condensed state of excitation light that is radiated, light can be easily detected. Furthermore, since the lens portion can be located nearer the sample, light to be dispersed can be reduced, and light can be easily extracted. Therefore, the sensitivity of the device can be increased. Additionally, since the lens portion is integrally formed with the bottom of the sample container, this contributes to the downsizing of the optical system.

DETAILED DESCRIPTION OF THE PREFERRED EMBODIMENTS

Figures 1A, 1B:
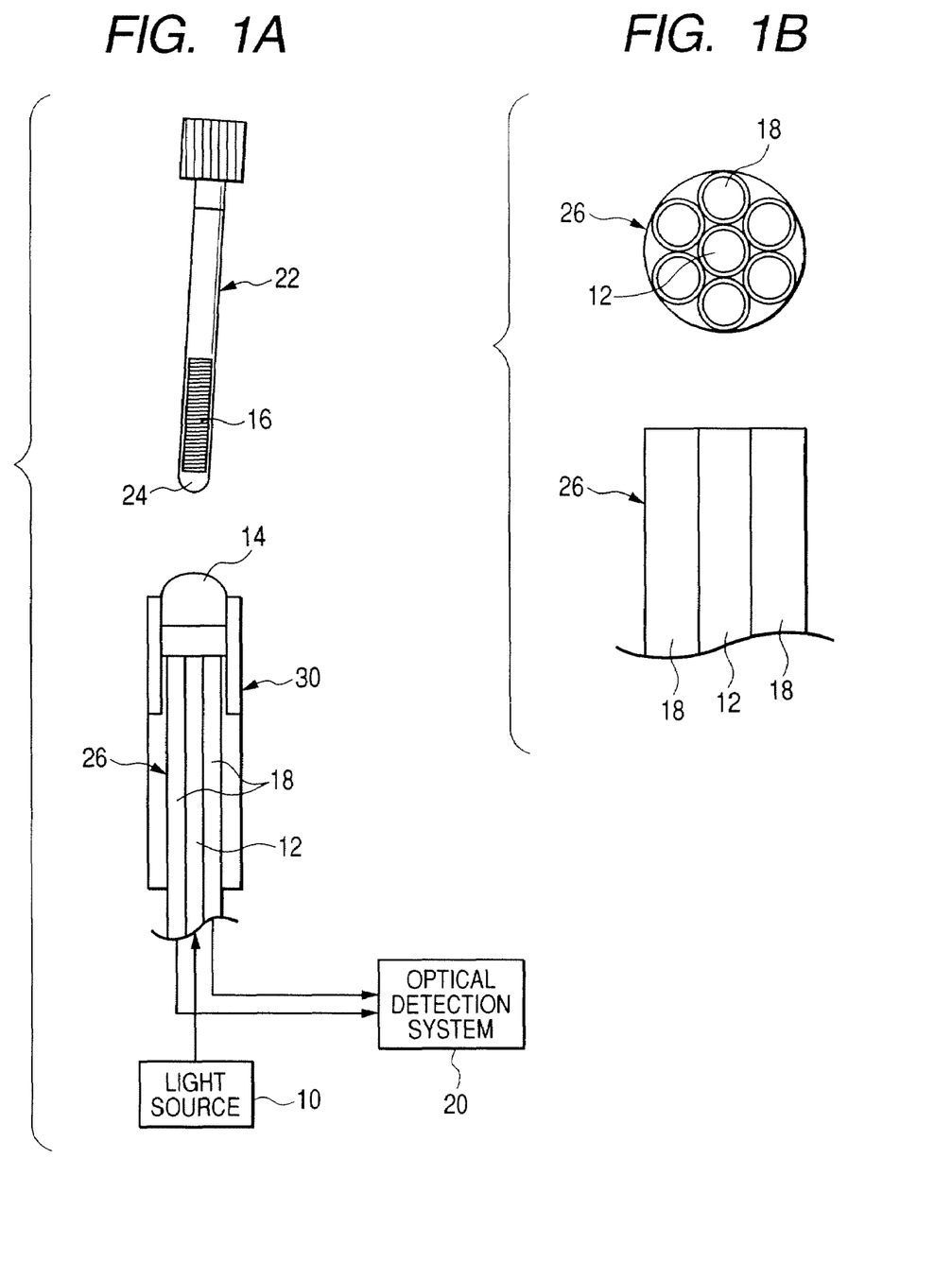
FIGS. 1A and 1B are diagrams for explaining an optical coupling system for a fluorescence measuring device and a sample according to the present invention.

An example optical coupling system of the invention for a fluorescence measuring device, and a sample, is shown in FIGS. 1A and 1B. As shown in FIG. 1A, the fluorescence measuring device is designed so that excitation light, emitted by a light source 10, is guided through an optical fiber 12, as an excitation light optical fiber of the invention, a sample 16 is irradiated, with the excitation light, through a coupling lens 14, fluorescence output by the sample 16 is received from the coupling lens 14 and is guided, through an optical fiber 18 used for receiving light, to an optical detection system 20. A sample container 22, where the sample 16 is retained, is so structured that a semispherical lens portion 24, for collecting excitation light and fluorescence, is integrally formed at the bottom of a transparent cylindrical body. The excitation light is changed to parallel light or converged light by the coupling lens 14, and is collected at the sample 16 by the lens portion 24.

In this example, six optical fibers 18, used for receiving light, are disposed around the periphery of one optical fiber 12, as the excitation light optical fiber, in the center, and these optical fibers are formed into a single optical fiber bundle (bundled fiber) 26 (see FIG. 1B). A capillary 30 is attached to the distal end of the optical fiber bundle 26, and a coupling lens 14 is inserted into and positioned within the capillary 30.

The sample container 22, wherein the lens portion 24 is integrally formed with the cylindrical body, can be obtained by employing the following manufacturing method. For example, a cylindrical body having a thick bottom is prepared and is inserted into a pipe-shaped holding tool. In this state, the cylindrical body is ground into a semispherical shape and finished by a spherical grindstone. Or, as another method, a semispherical lens portion is separately fabricated and adhered to the bottom of the cylindrical body.

In this example, the optical coupling system of the light measuring device and the sample is constituted by the optical fibers 12 and 18, the coupling lens 22 and the lens portion 24 of the sample container 22. Excitation light, emitted by the light source 10, is guided through the excitation light optical fiber, and is collected by the coupling lens 14 and the semispherical lens portion 24, so that the sample 16 in the sample container 22 is irradiated with the excitation light. Fluorescence output by the sample 16 is then passed through the lens portion 24 and the coupling lens 14, and is guided to the optical detection system 20 by the light fiber 18 used for receiving light.

Since the sample container 22 is so designed that the semispherical lens portion 24 is integrally formed with the cylindrical bottom, the sample 16 can be efficiently irradiated with excitation light, and fluorescence can be efficiently extracted. Compared with when only the coupling lens 14 is employed, the excitation light used to irradiate the sample 16 is more concentrated, and the radiation density of the excitation light is increased, so that a greater amount of florescence is output by the sample 16. Further, since the lens portion 24 can be arranged so it is nearer the sample 16, the dispersal of fluorescence is reduced, and since the state of fluorescence can be similar to the state of a point source in consonance with the collected state of excitation light to be emitted, fluorescence can be more easily detected. Furthermore, since the lens portion 24 is integrally formed with the sample container 22, the size of the system can be reduced.

Figure 2:
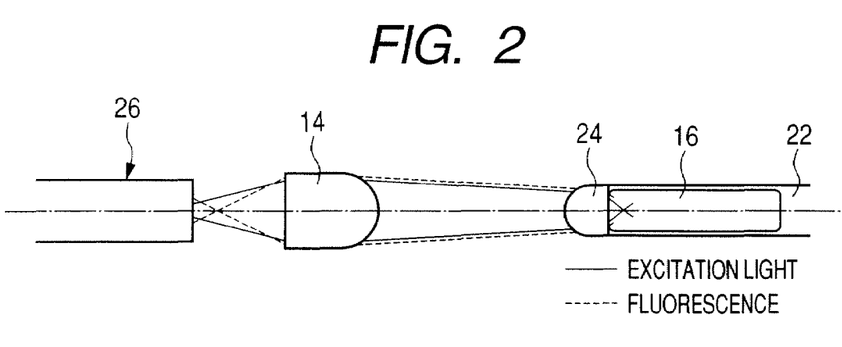
FIG. 2 is an explanatory diagram showing an optimal arrangement and the transmission state of excitation light.

The optimal optical arrangement and the excitation light transmission state are shown in FIG. 2. It should be noted that the light axis is shown transversely. In this example, the coupling lens 14 and the lens portion 24, at the bottom of the sample container 22, are so arranged that these two components do not contact each other, i.e., are separated, located at a distance, and a light collecting point will not be formed between them. At this time, it is preferable that the optical fibers 12 and 18 of the optical fiber bundle 26, the coupling lens 14 and the sample container 22, to which the lens portion 24 is attached, satisfy the following conditions. First, when the excitation light (indicated by a solid line) transmitted through the optical fiber 12 enters the lens portion 24 of the sample container 22, eclipsing of the light should be avoided, and it is preferable that the coupling lens 14 change the excitation light to parallel light or converged light before emitting it to the lens portion 24. Second, the focal point for the excitation light, which passes through the lens portion 24 before entering the sample container 22, should be located within the sample 16, the length of which depends on the volume of the sample container 22, and should be as near the lens portion 24 as possible. Third, fluorescence, indicated by broken lines, should be collected by using numerical aperture (NA) that is equal or smaller than the number of optical fiber end faces, so that fluorescence, as it is produced, is diffused to locations whereat the end faces of the optical fibers are positioned, within a range wherein optical fibers for receiving fluorescence are present. When, for example, as shown in FIG. 1B, a plurality of optical fibers for receiving fluorescence are circumferentially arranged, fluorescence can be collected within a range equal to or smaller than a circle encompassing the end face of each optical fiber. Thus, the loss of excitation light can be reduced, and the sample 16 can be irradiated by excitation light having a high radiation density. Further, fluorescence can be condensed by using the maximum NA for the lens portion 24 of the sample container 22, and the coupling loss of fluorescence can be reduced.

When, as shown in FIGS. 1A and 1B, the optical fiber 12 for excitation light and the optical fibers 18 for receiving light are bundled to form the optical fiber bundle 26, it is preferable that an outer diameter φF of the optical fiber bundle 26<diameter φL of the coupling lens 14, and the diameter of the optical fiber 12 for excitation light≦the diameter of an optical fiber 18 for receiving fluorescence, and that excitation light be transmitted inside and fluorescence be transmitted outside. Thus, eclipsing of excitation light by the coupling lens 14 can be avoided, and the sample 16 can be efficiently excited. When the diameter of the excitation light optical fiber 12 is reduced, the image of excitation light formed by the coupling lens 14 becomes smaller, so that the radiation density of the excitation light is increased and the sample 16 is efficiently excited. Further, since the shape of fluorescence becomes more similar to that emitted by a point source, the extraction of fluorescence is easy. In addition, the coupling lens 14 that employs the capillary 30 and the optical fiber bundle 26 can be integrated (assembled).

As shown in FIG. 1A, the sample container 22 to which the lens portion 24 is attached may be arranged so it is inclined several degrees from the light axis of the coupling lens 14. In this case, the arrangement is shifted in consonance with the inclination of the sample container 22 to which the lens portion 24 is attached.

EMBODIMENTS

An appropriate optical arrangement, the transmission states of excitation light and fluorescence and a beam profile were obtained by using the optical coupling system shown in FIGS. 1A and 1B. As described above, the optical coupling system includes: an optical fiber bundle (bundled fiber) 26, formed of a plurality of optical fibers for transmitting excitation light and fluorescence; a coupling lens 14, for passing excitation light from the optical fiber bundle 26 to the sample 16, or for passing fluorescence from the sample 16 to the optical fiber bundle 26; and a sample container 22 to which a lens portion 24 is attached.

A bundle of seven step index silica fibers having core diameters of 200 μm and NA=0.2 was employed as an optical fiber bundle. As shown in FIG. 1B, one fiber in the center was employed as an optical fiber for the transmission of excitation light, and the six fibers around it were employed as optical fibers for the transmission of fluorescence. The diameter of a circle encompassing the optical fiber bundle is 2.78 mm.

A planoconvex lens of φ=2.4 mm and f=2.9 mm was employed as the coupling lens 14. The shape of the coupling lens 14 is not especially limited to a planoconvex lens; however, it is preferable that the diameter of a lens be smaller than that of the optical fiber, and that the thickness of the round edge (thickness of the flat plate portion of a lens) also be greater, because the assembling process, for integrating a coupling lens and an optical fiber bundle, is simplified. In order to prevent excitation light from being reflected by the surface of the lens and becoming noise, and to prevent fluorescence from being reflected by the surface of the lens and causing transmission loss, reflection attenuation coatings, for an excitation wavelength and for a fluorescence wavelength, were applied to both surfaces of the lens.

As shown in FIG. 1A, the coupling lens 14 and the optical fiber bundle were positioned and secured by being passed through the capillary. At this time, the face of the coupling lens near the optical fiber end face was a flat face, while the face near the sample was a convex face, and the distance between the flat lens face and the end face of the optical fiber bundle was about 2.1 mm, in the light axial direction.

Fluoresceinisothiocyanate FITC was employed as a sample, and about 10 μL of it was enclosed in a glass sample container having a diameter of about 1.5 mm by appropriately adjusting the density. A semispherical lens portion having a diameter of about 1.5 mm, which is the same as that of the sample container, and r=about 0.7 mm was integrally formed at the bottom of the sample container. It is preferable that reflection attenuation coatings for an excitation wavelength and for a fluorescence wavelength also be applied to the lens portion of the sample container.

A wavelength selection filter was employed that permits only a wavelength 470±10 nm to pass, and light was extracted from light emitted by a light emitting diode (LED) that has a light emission peak near a wavelength 470 nm. This extracted light was employed as excitation light. This light was connected to the excitation light optical fiber included in the optical fiber bundle. Excitation light, having with a beam diameter substantially equal to the size of the lens portion, is output at the end face of the excitation light optical fiber, passes through the coupling lens, enters the lens portion at the bottom of the sample container, and is converged at a location deep inside the sample, measured from the bottom of the sample container. Fluorescence is generated from the entire range where excitation light is transmitted, primarily at the focal position of excitation light. Fluorescence, which is connected to the optical fibers by the lens portion of the sample container and the coupling lens, is separated by a wavelength filter that permits only a desired wavelength, one that is to be detected (532 nm in this case), to pass. Then, the resultant light is transmitted to an optical detector module (a photomultiplier), and is converted into an electric signal.

Figure 3A:
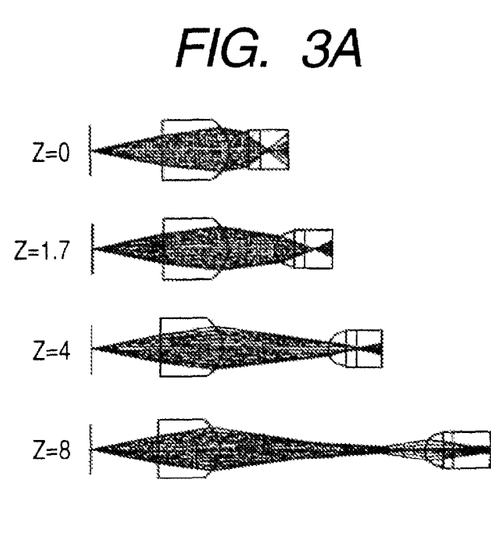
FIGS. 3A and 3B are diagrams showing simulations for rays when a distance z between the convex face of a coupling lens and the convex face of a lens portion in the light axial direction is varied.
Figure 3B:
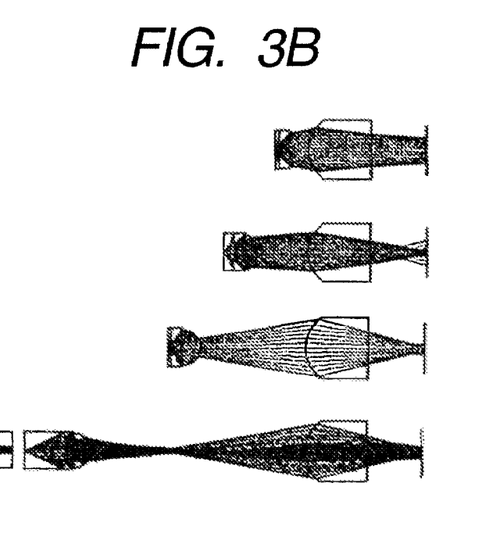
Figure 4A:
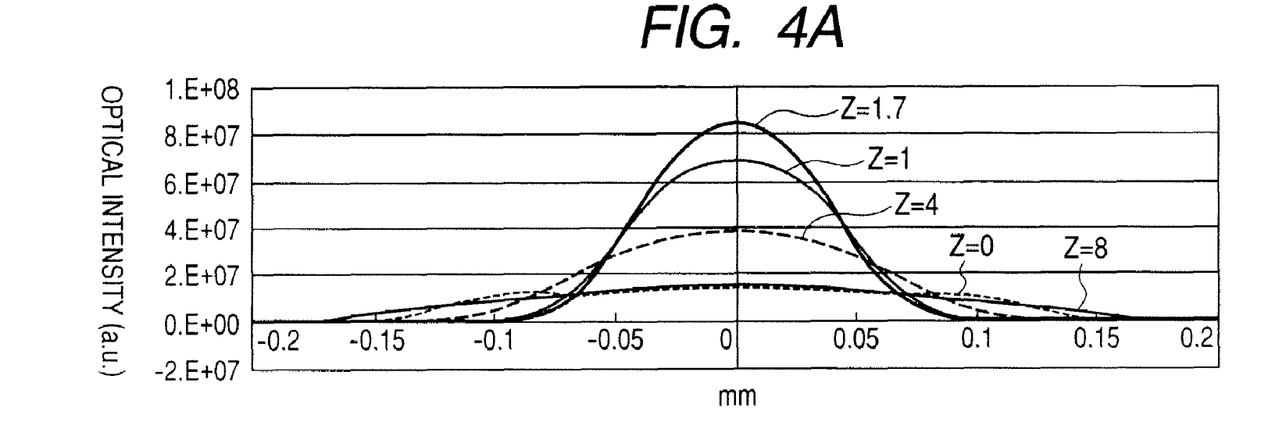
FIGS. 4A and 4B are diagrams showing the beam profiles of excitation light and fluorescence when the distance z, in the light axial direction, is varied.
Figure 4B:
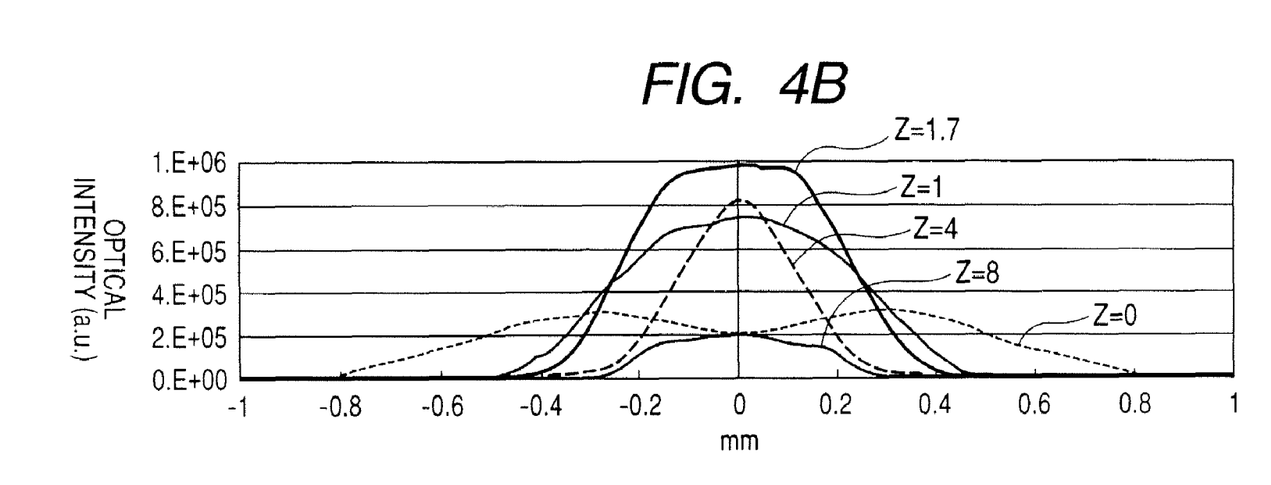

FIGS. 3A and 3B are diagrams showing simulation results for rays when a distance z, between the convex face of the coupling lens and the convex face of the lens portion in the light axial direction, is varied. FIGS. 4A and 4B are diagrams showing beam profiles for excitation light and fluorescence when the distance z in the light axial direction is varied. As is apparent from these results, when the sample container to which the lens portion is attached is located at a distance of about 1.7 mm from the convex face of the coupling lens in the light axial direction, the peak intensity of excitation light is the highest, and excitation light is condensed best. Further, it is also found that, when z=1.7 mm, the intensity of fluorescence is the highest and fluorescence converges within a range (about 0.7 mm) wherein the receiving light optical fibers are present. In this case, the excitation light passes through the coupling lens, enters the lens portion of the sample container, which has a beam diameter of about 1.5 mm that is substantially equal to the size of the lens portion, and converges at a location about 0.8 mm deep, inside the sample, from the bottom of the sample container.

On the other hand, when the coupling lens and the lens portion of the sample container contact each other (z=0 mm), and when the coupling lens and the lens portion of the sample container are separated, located at a distance, and a light collecting point is formed (e.g., z=8 mm), it is found that the peak intensity of excitation light is extremely low and excitation light is almost not collected, and that the intensity of fluorescence is also low, or fluorescence is broadly spread. According to these results, the distance z between the convex face of the coupling lens and the convex face of the lens portion in the light axial direction should be set at from 1 mm to 4 mm (more preferably, 1.7±0.7 mm, while 1.7 mm is optimal).

Comparison Results

Figure 5A:
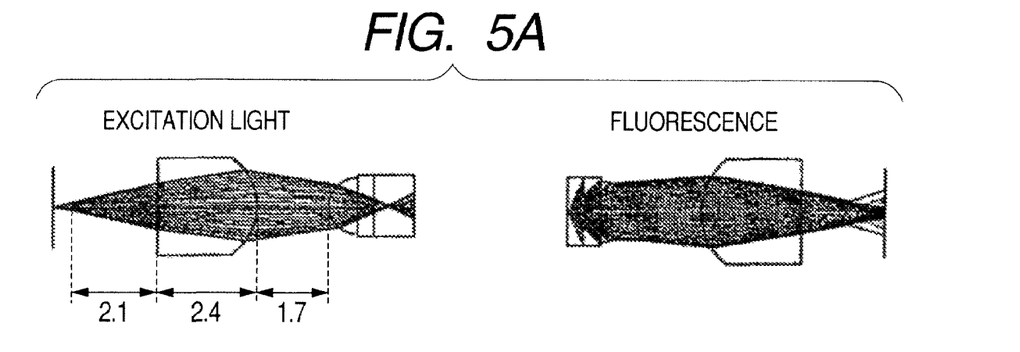
FIGS. 5A and 5B are diagrams showing simulations for transmissions of excitation light and fluorescence.
Figure 5B:
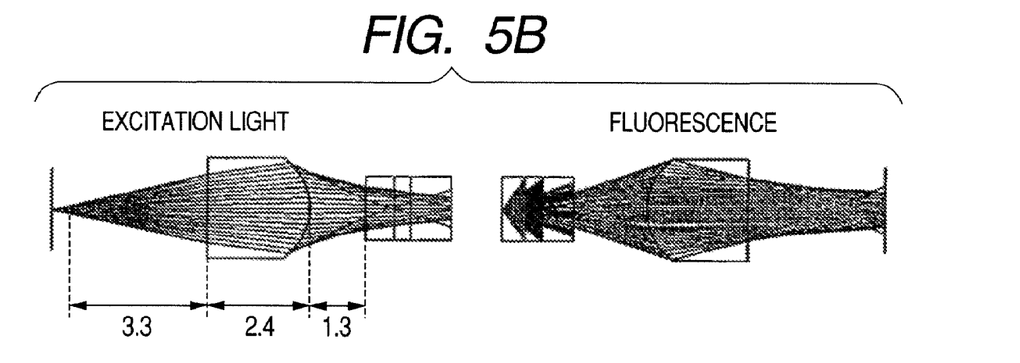

A case (the present invention) wherein the lens portion was provided for the sample container and a case (a conventional example) wherein condensing means was not provided for the sample container were compared. The present invention case was the optimal state, wherein a sample container to which a lens portion was attached was located at a distance of about 1.7 mm, in the light axial direction, from the convex face of a coupling lens. FIGS. 5A and 5B are diagrams showing the simulation results obtained for the transmission of excitation light and fluorescence. The light transmission characteristics in the two cases are shown in Table 1.

TABLE 1

|  | present invention (with lens portion) | Comparative example (no lens portion) |
| --- | --- | --- |
| (a) Transmission of excitation light | 0.6421 a.u. | 0.6246 a.u. |
| (b) Transmission of fluorescence | 0.0942 a.u. | 0.0109 a.u. |
| (c) Amount of detected fluorescence: (a) * (b) | 0.0605 a.u. 76 mV | 0.0068 a.u. 8.6 mV |

The amount 76 mV of fluorescence detected for this invention is an actual value observed by a photomultiplier with an excitation light of 9.2 µW and an FITC density of 1 pmol/10 µL. The amount 8.6 mV of fluorescence detected in the comparative example is a value calculated based on the amount 76 mV for the invention (the amount of fluorescence detected in the case wherein a lens portion was not used/the amount of detected fluorescence in the case wherein a lens portion was used).

As shown in Table 1, when the present invention case (the lens portion was mounted on the sample container) is compared with the comparative example case (the lens portion was not provided for the sample container), it is found that, in the present invention case, about nine times the fluorescence can be detected.

Figure 6A:
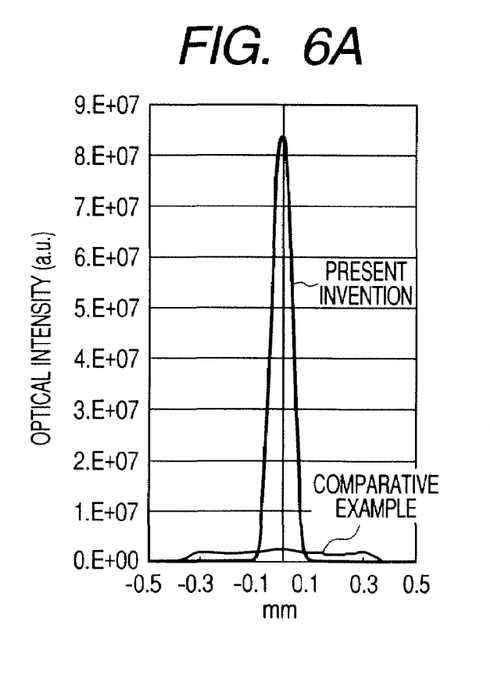
FIGS. 6A and 6B are diagrams showing beam profiles for the focal position of an excitation light and beam profiles for a fluorescence receiving position.
Figure 6B:
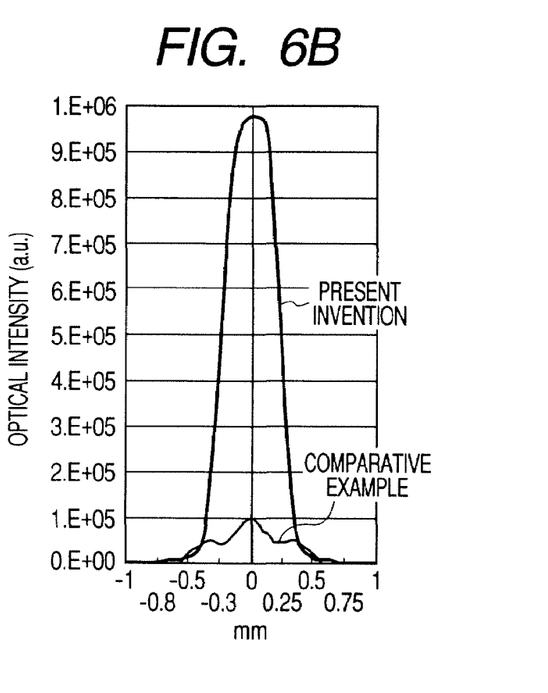

FIGS. 6A and 6B are diagrams showing beam profiles at the focal position for excitation light and beam profiles at a fluorescence receiving position. As is apparent from these beam profiles, when a lens portion was not provided for the sample container (the comparative example), excitation light could not be concentrated and a sufficient intensity for excitation light could not be obtained (only weak and spreading excitation light was obtained). Furthermore, when a lens portion was not provided for the sample container (the comparative example), the spread angle of fluorescence was large, so that only small amount of fluorescence was collected by the coupling lens. On the other hand, when a lens portion was attached to the sample container (the present invention), excitation light could be concentrated, and a sufficient intensity for excitation light could be obtained. Additionally, it was found that the spread angle of fluorescence was small, and a very large amount of fluorescence was collected by the coupling lens.

Also, when a lens portion was not provided for the sample container, in order to efficiently collect fluorescence, the distance between the coupling lens and the sample container was reduced and the distance between the optical fiber and the coupling lens was extended, so that adjustment of the positions of the optical fiber and the coupling lens was difficult (since excitation light employed almost the entire face of the coupling lens, eclipsing of light tended to occur as a result of only a small position difference). On the other hand, according to this invention, since the distance between the optical fiber and the coupling lens is reduced, the positions of the optical fiber and the coupling lens could be easily adjusted.

Figures 7A, 7B:
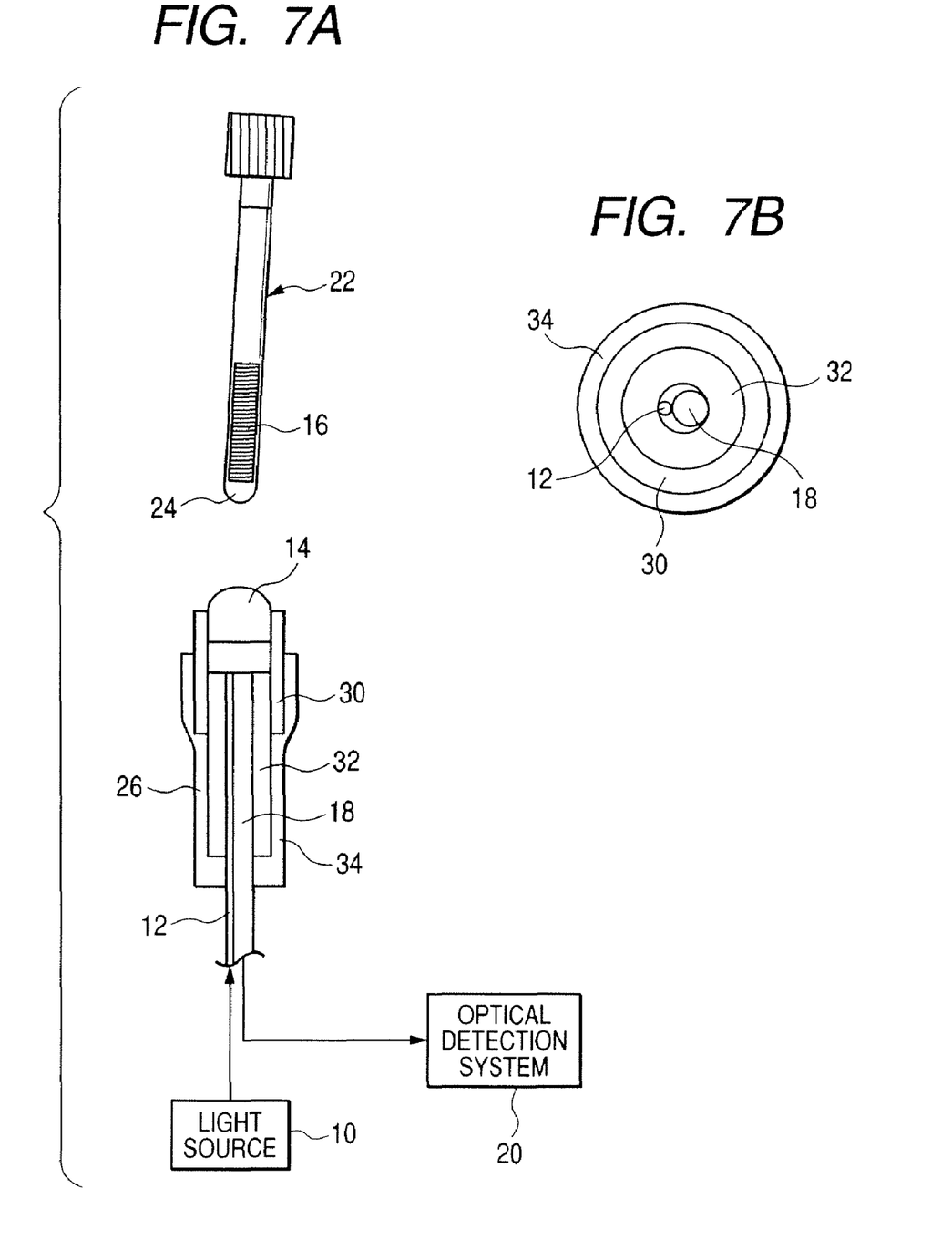
FIGS. 7A and 7B are diagrams for explaining an optical coupling system for a fluorescence measuring device and a sample according to the present invention.

In this embodiment, the optical fiber bundle has been employed. However, a plurality of optical fibers are not always necessary to receive fluorescence, and only a single optical fiber may be employed. Such an embodiment is shown in FIGS. 7A and 7B. In this embodiment, one optical fiber 12 for excitation light and one optical fiber 18 for receiving light are adjacently arranged and are inserted through a ferrule 32 and fixed. A capillary 30 is attached to the distal ends of the optical fibers, and a coupling lens 14, used for excitation light and fluorescence, is inserted into the capillary 30 and is positioned and secured therein. The outer walls of the capillary 30 and the ferrule 32 are covered with a protective tube 34.

Here, a step index silica fiber having a core diameter of 200 µm, a clad diameter of 250 µm and NA=0.2 is employed for an excitation light optical fiber, and a grated index fiber having a core diameter of 600 µm, a clad diameter of 750 µm and NA=0.2 is employed for a receiving light optical fiber. A cylindrical ferrule is employed and the diameter of the center through hole is 1.0 mm. Therefore, the center of the excitation light optical fiber is located at a distance of 0.375 mm from the center of the ferrule, while the center of the receiving light optical fiber is located at a distance of 0.5 mm from the center of the excitation light optical fiber, with the center of the ferrule in between. That is, the center of the receiving light optical fiber is located at a distance of 0.125 mm from the center of the ferrule.

A planoconvex lens with φ=2.4 mm and f=2.9 mm, which are the same as those in the previous embodiment, is employed as a coupling lens. On the surface of the coupling lens, reflection attenuation coatings are applied for an excitation wavelength and a fluorescence wavelength. The coupling lens and the optical fibers are positioned and secured by being inserted through a capillary. At this time, the flat face of the coupling lens is directed toward the optical fiber, while the convex face is directed toward the sample, and the distance between the coupling lens and the end face of the optical fiber is 2.1 mm in the light axial direction.

The same measurement was conducted for the same reagent used for the previous embodiment. It was found that when the distance z, in the light axial direction, was about 0.5 mm and the reagent was irradiated by excitation light of 11.3 φW, a fluorescence intensity of 8 pW was obtained by an optical power meter, and an extremely small amount of fluorescent signals could be efficiently measured. At this time, since the center of the excitation light optical fiber and the center of the receiving light optical fiber are shifted away from the center of the coupling lens, in accordance with the shifting distance, the arrangement of the components is shifted perpendicular to the z axis.

According to this embodiment, an explanation has been given only for a case wherein there is an excitation light wavelength of 470±10 nm and a detected fluorescence wavelength of 532±20 nm. The present invention is not limited to these wavelengths, and can be applied for any wavelength when a light source, a wavelength selection filter for excitation light and a wavelength selection filter for fluorescence are changed in accordance with the excitation spectrum and the fluorescence spectrum of a sample. For example, PE-Cy5 (R-Phycoerythrin/Cy5 tandem pigment) can be measured by setting a wavelength of 470±10 nm for excitation light and a wavelength of 670±20 nm for light to be detected. Further, Texas Red can be measured by setting a wavelength of 532±10 nm for excitation light and a wavelength of 640±20 nm for light to be detected.

What is claimed is:

1. An optical system coupling a light measuring device and a sample, wherein excitation light emitted by a light source is guided through an excitation light optical fiber to irradiate the sample, and excited light emitted by the sample is guided to an optical detection system through a receiving light optical fiber, the optical system comprising:
    a light measuring device including
        an excitation light optical fiber for guiding an excitation light to irradiate a sample,
        a receiving light optical fiber for receiving excited light from the sample, and
        a coupling lens arranged on a sample side of the excitation light optical fiber and the receiving light optical fiber; and
    a sample container including a cylindrical body for retaining the sample to which the excitation light is irradiated, and
        a lens portion integrally formed on a bottom of the cylindrical body for collecting the excitation light and the light emitted from the sample;
    wherein the excitation light is changed to parallel light or converged light by the coupling lens and collected at the sample by the lens portion.

2. An optical coupling system according to claim 1, wherein a distal end of an optical fiber bundle, which is provided with the excitation light optical fiber which is centered in the optical fiber bundle and a plurality of the receiving light optical fibers surround the excitation light optical fiber, is retained by a capillary, and
    the coupling lens is inserted into the capillary.

3. An optical coupling system according to claim 1, wherein the excitation light optical fiber and the receiving light optical fiber are adjacently fixed through a ferrule, and
    distal ends of the excitation light optical fiber and the receiving light optical fiber are attached to a capillary, and
    the coupling lens is inserted into the capillary.

4. An optical coupling system according to claim 1, wherein a diameter of the excitation light optical fiber is equal to or smaller than a diameter of the receiving light optical fiber.

5. An optical coupling system according to claim 1, wherein the coupling lens and the lens portion are arranged at a distance to prevent formation of a light collecting point between the coupling lens and the lens portion.

* * * * *